(12) United States Patent
Afriat

(10) Patent No.: US 6,799,380 B2
(45) Date of Patent: Oct. 5, 2004

(54) TEMPLATE FOR A MODULAR JOINT PROSTHESIS COMPONENT

(76) Inventor: Jacques Afriat, Polyclinique du Languedoc, Route de Narbonne Plage, Narbonne (FR), 11100

( * ) Notice: Subject to any disclaimer, the term of this patent is extended or adjusted under 35 U.S.C. 154(b) by 0 days.

(21) Appl. No.: 10/446,674

(22) Filed: May 29, 2003

(65) Prior Publication Data

US 2004/0107594 A1 Jun. 10, 2004

(30) Foreign Application Priority Data

Dec. 1, 2000 (GB) .............................................. 0029317
Nov. 30, 2001 (WO) .............................. PCT/GB01/05296

(51) Int. Cl.$^7$ ............................ G01B 3/14; A61B 17/56
(52) U.S. Cl. ........................... 33/562; 33/512; 606/102; 623/912
(58) Field of Search .......................... 33/511, 512, 562; 606/53, 86, 102; 623/16.11, 18.11, 909, 912

(56) References Cited

U.S. PATENT DOCUMENTS

| | | | | | |
|---|---|---|---|---|---|
| 3,815,590 A | * | 6/1974 | Deyerle | ...................... | 606/102 |
| 4,594,792 A | * | 6/1986 | Cramb | ........................ | 33/562 |
| 4,630,375 A | * | 12/1986 | Spolyar | ........................ | 33/512 |
| 5,070,623 A | * | 12/1991 | Barnes | ........................ | 33/512 |
| 5,141,513 A | * | 8/1992 | Fortune et al. | ............... | 606/53 |
| 5,197,989 A | * | 3/1993 | Hinckfuss et al. | ........ | 623/22.42 |
| 5,331,744 A | * | 7/1994 | Rumsey | ........................ | 33/562 |
| 5,735,904 A | * | 4/1998 | Pappas | ........................ | 606/86 |
| 5,885,295 A | * | 3/1999 | McDaniel et al. | ............ | 606/86 |
| 2003/0236521 A1 | * | 12/2003 | Brown et al. | .................. | 606/80 |
| 2004/0034350 A1 | * | 2/2004 | St. Onge et al. | .............. | 606/60 |

* cited by examiner

Primary Examiner—G. Bradley Bennett

(57) ABSTRACT

A template for use in matching parts (6, 8) of a modular joint prosthesis component to an image of a bone in which the prosthesis component is to be implanted, the prosthesis component including first and second parts (6, 8) which are fitted together to assemble the prosthesis component for implantation. The template comprises a first template part which bears an image of the first part of the prosthesis component, and a second template part which bears images of a plurality of the second parts (23) of the prosthesis component, each of the second parts (23) being a sleeve having a through bore in which, in the assembled prosthesis component, the first part (6) of the prosthesis component can be received. The second template part is connected to the first template part but can be moved relative to it so that the images of the second parts (23) of the prosthesis component can be aligned sequentially in relation to the image of the first template part (6) to form a composite image of the prosthesis component.

10 Claims, 3 Drawing Sheets

TEMPLATE FOR A MODULAR JOINT PROSTHESIS COMPONENT

This invention relates to a template for use in matching parts of a modular joint prosthesis component to an image of the bone in which the prosthesis component is to be implanted.

Successful implantation of a component of a joint prosthesis in a cavity in a bone requires that the component fits accurately within the cavity. Selection of a component for a patient can be done with reference to pre-operation images that are prepared of the bone. Such images can be prepared using, for example, X-ray apparatus. Selection of the component can then be done by holding available components or images of them against the bone image.

In order to provide a surgeon with a range of components with different configurations, it is known to provide joint prosthesis components which have a modular construction. In this way, components can be assembled for implantation with a configuration which matches the patient's bone cavity as closely as possible, while the inventory of components that has to be produced is kept smaller than would be the case if separate components had to be produced for each configuration.

Difficulties can however arise when a pre-operation image is relied on when selecting parts of a multi-part prosthesis component. Conventionally, an X-ray image of the bone is held against a vertical light box. It can then be difficult to manipulate the prosthesis component parts, or images against them, in proper alignment against the X-ray image.

The present invention provides a template which comprises first and second template parts, which bear images of first and second component parts respectively, and which are connected but can be moved relative to one another so that the images of the second parts of the prosthesis component are positioned sequentially over the image of the first template part to form a composite image of the prosthesis component.

Accordingly, in one aspect, the invention provides a template for use in matching parts of a modular joint prosthesis component to an image of a bone in which the prosthesis component is to be implanted, the prosthesis component comprising a first part and a second part which are fitted together to assemble the prosthesis component for implantation, which comprises:

a. a first template part which bears an image of the first part of the prosthesis component, and
b. a second template part which bears images of a plurality of the second parts of the prosthesis component, each of the second parts being a sleeve having a through bore in which, in the assembled prosthesis component, the first part of the prosthesis component can be received, in which the second template part is connected to the first template part but can be moved relative to it so that the images of the second parts of the prosthesis component are aligned sequentially in relation to the image of the first template part to form a composite image of the prosthesis component, one of the template parts overlying the other of the template parts and being transparent so that the image on the said other template part is visible through the overlying template part when the images on the template parts are aligned.

The template of the present invention has the advantage that it can greatly simplify the use of a template in the selection of the parts of a multi-part prosthesis component when used in conjunction with an image of the bone in which the prosthesis component is to be implanted, because images of the prosthesis component parts are connected to one another and need not be held separately against the bone image. It is therefore possible that the surgeon is only required to manipulate the template of the invention as a single article in addition to the bone image, which can enable the surgeon to compare the configuration of the bone with the configurations of assembled prosthesis components with several different effective configurations. The greater ease with which the surgeon is able to use the template of this invention can therefore assist in the proper selection of a prosthesis component for implantation, and therefore reduce surgical error.

The first and second template parts can be connected to one another directly, for example when the template consists of just those two parts. The template parts might however be connected indirectly, for example by each of them being mounted on a connecting support.

The second template part is mounted so that it can be moved relative to the first template part, so that the images of the second parts of the prosthesis component are positioned sequentially in relation to the image of the first template part to form a composite image of the prosthesis component. The nature of the movement might involve, for example, sliding the second template part along a guide, for example defined by a fastening strip. Preferably however the second template part is mounted so that its movement relative to the first template part involves rotation. For example, the second template part might then be fastened at a point by a fastener such as a rivet, for rotation about that point.

Preferably, the first template part bears images of two (or more) views of the first part of the prosthesis component. This will enable improved matching of the prosthesis component to the bone cavity, using images of the bone cavity which correspond to the images of the component. For example, the views of the component might be elevational outline views along the medial-lateral and anterior-posterior axes, which can be aligned with images of the bone cavity along the corresponding axes.

Accordingly, in another aspect, the invention provides a template for use in matching parts of a modular joint prosthesis component to an image of a bone in which the prosthesis component is to be implanted, the prosthesis component comprising a first part and a second part which are fitted together to assemble the prosthesis component for implantation, which comprises:

a. a first template part which bears images of two views of the first part of the prosthesis component, and
b. a second template part which bears images of two views of each of a plurality of the second parts of the prosthesis component, in which the second template part is connected to the first template part but can be moved relative to it so that the images of the views of the second parts of the prosthesis component are positioned sequentially in relation to the images of the corresponding views of the first template part to form composite images of the two views of the assembled prosthesis component.

When the first template part bears images of at least two views of the first part of the prosthesis component, it will be preferred for the second template part to bear images of two views of at least some, preferably each, of the second parts of the prosthesis component. When the second template part is mounted for rotation relative to the first template part, and the images of the views of any one of the second parts of the prosthesis component are preferably arranged approximately equidistant from the axis of rotation of the second template part, for example diametrically opposite to one another on the second template part.

Preferably, the template of the invention includes a third template part which bears images of a plurality of third parts of the prosthesis component. Preferably, the third template part is connected to the first template part but can be moved relative to it, so that the images of the third parts of the prosthesis component are positioned sequentially in relation to the image of the first template part to form a composite image of the prosthesis component.

When one of the template parts overlies the other template part, it is preferably transparent, at least in part, so that the said other image is visible (at least partly) through the overlying image. For example, the overlying template part might comprise a transparent polymeric material such as a polyester. The other template part can also be transparent, particularly when the template is intended to overlie the image of a bone. For other arrangements, the other template might be essentially opaque. It will generally be preferred however that it be made from a polymeric material, whether transparent or opaque, especially a polyester or a polyamide.

Markings on the template parts, principally the images of the component parts, can be provided by printing, using a material which is suitably resistant to being displaced, for example by washing or abrasion. Suitable techniques such as printing and materials will be known, depending in part on the materials which are used for the template parts.

The template of the invention is envisaged for use in particular with any prostheses in which a component comprises at least two parts which can be fitted together to provide the prosthesis component. It finds particular application when used in conjunction with the femoral component of a hip joint prosthesis, or with the humeral component of a shoulder joint prosthesis. For example, the first component part might be the stem part of a femoral component or a humeral component and the second component might be a collar part which fits around the stem part at or towards its proximal end. One of the component parts might be the head part of a femoral or a humeral component, which acts against the corresponding cup component of the joint prosthesis, especially when the prosthesis component comprises three or more parts (distal stem part, proximal neck stem part, collar part and head part).

Techniques by which the parts of the prosthesis component fit together to form the assembled prosthesis are known in relation to known modular prosthesis components.

The invention will now be described by way of example with reference to the accompanying drawings, in which.

Figure 1:
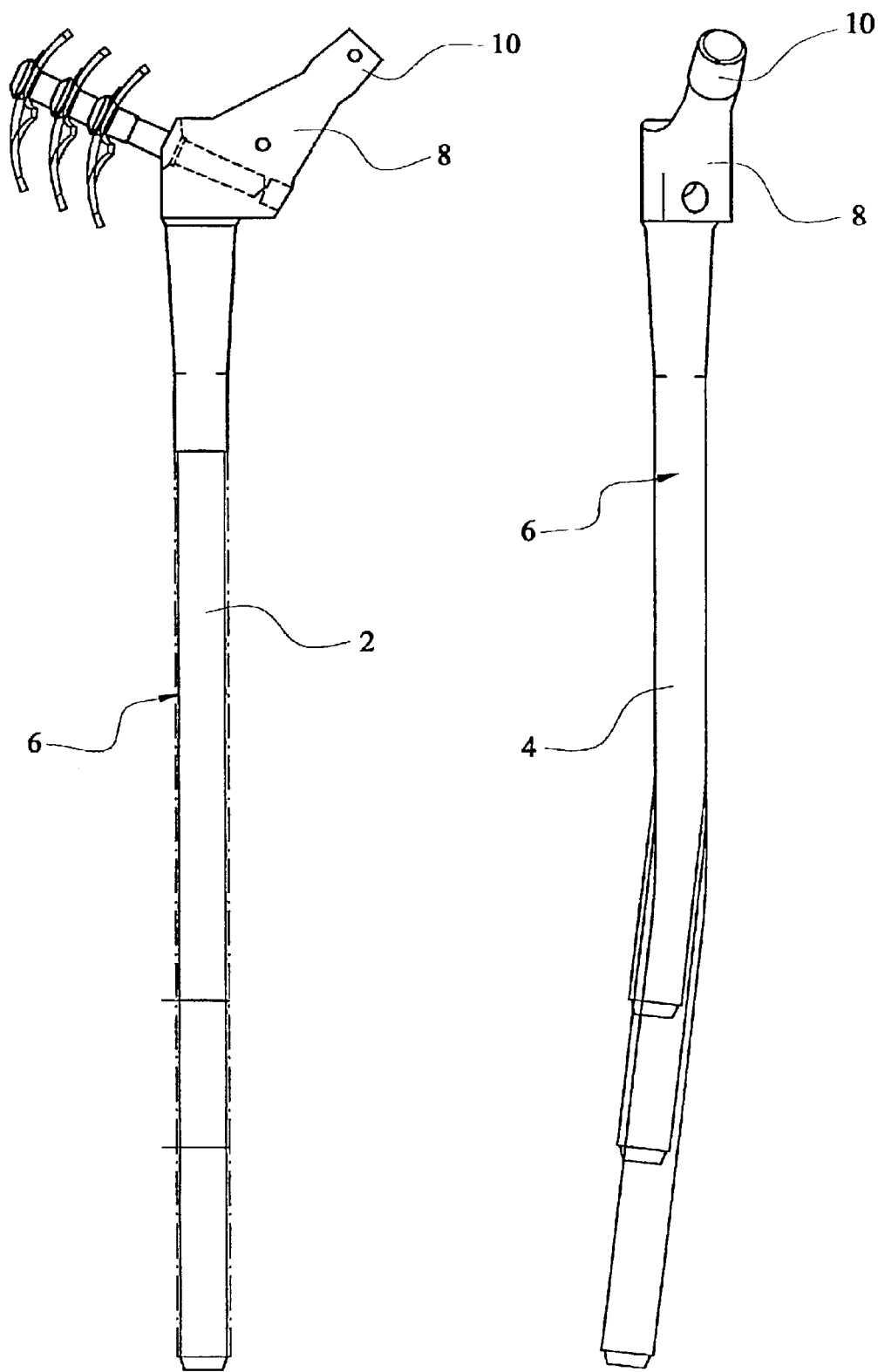
FIG. 1 is a view of a first template part.

Referring to the drawing, the first template part shown in FIG. 1 has on it A-P and M-L views 2, 4 of a stem part 6 of a hip joint femoral prosthesis. The prosthesis part comprises a stem 6 which can be implanted within the intramedullary canal of a femur, and a head portion 8. The head portion includes a tapered spigot 10 which can be received in a correspondingly tapered socket in a head part (not shown). The head part is then received in the acetabular cup component of the hip joint prosthesis.

Figure 2:
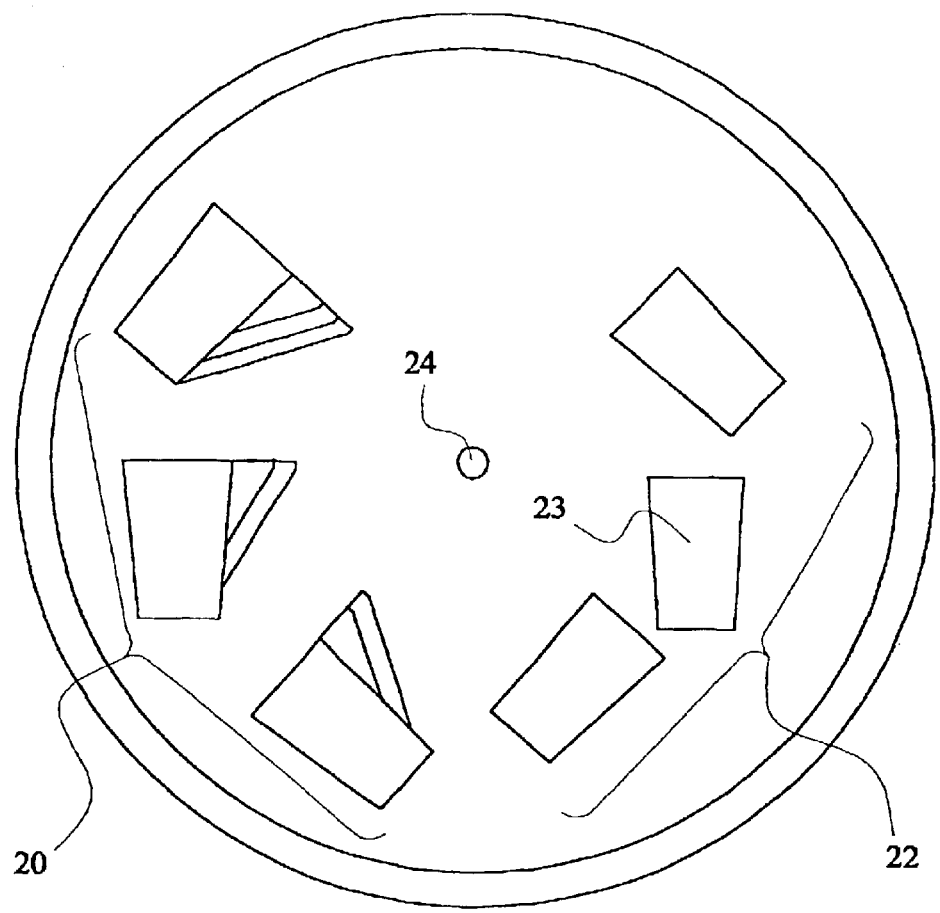
FIG. 2 is a view of a second template part.

FIG. 2 shows a second template part which has on it A-P and M-L views 20, 22 of a shoulder part 23 of the hip joint femoral prosthesis. The shoulder part fits onto the stem part towards the head portion: it has a bore extending through it into which the stem part can be inserted.

The shoulder parts on the second template part have three different sizes. The A-P views of the different sizes of the second template part are arranged at a common distance from a pivot point 24 on the second template part. Similarly, the M-L views of the different sizes of the second template part are arranged at a common distance from the pivot point (which could be the same as the distance of the A-P views). The views are so arranged that the A-P and M-L views of each of the three second template parts are positioned diametrically opposite to one another.

The second template part is made from a transparent plastic material, which has the views of the prosthesis part printed onto it.

Figure 3:
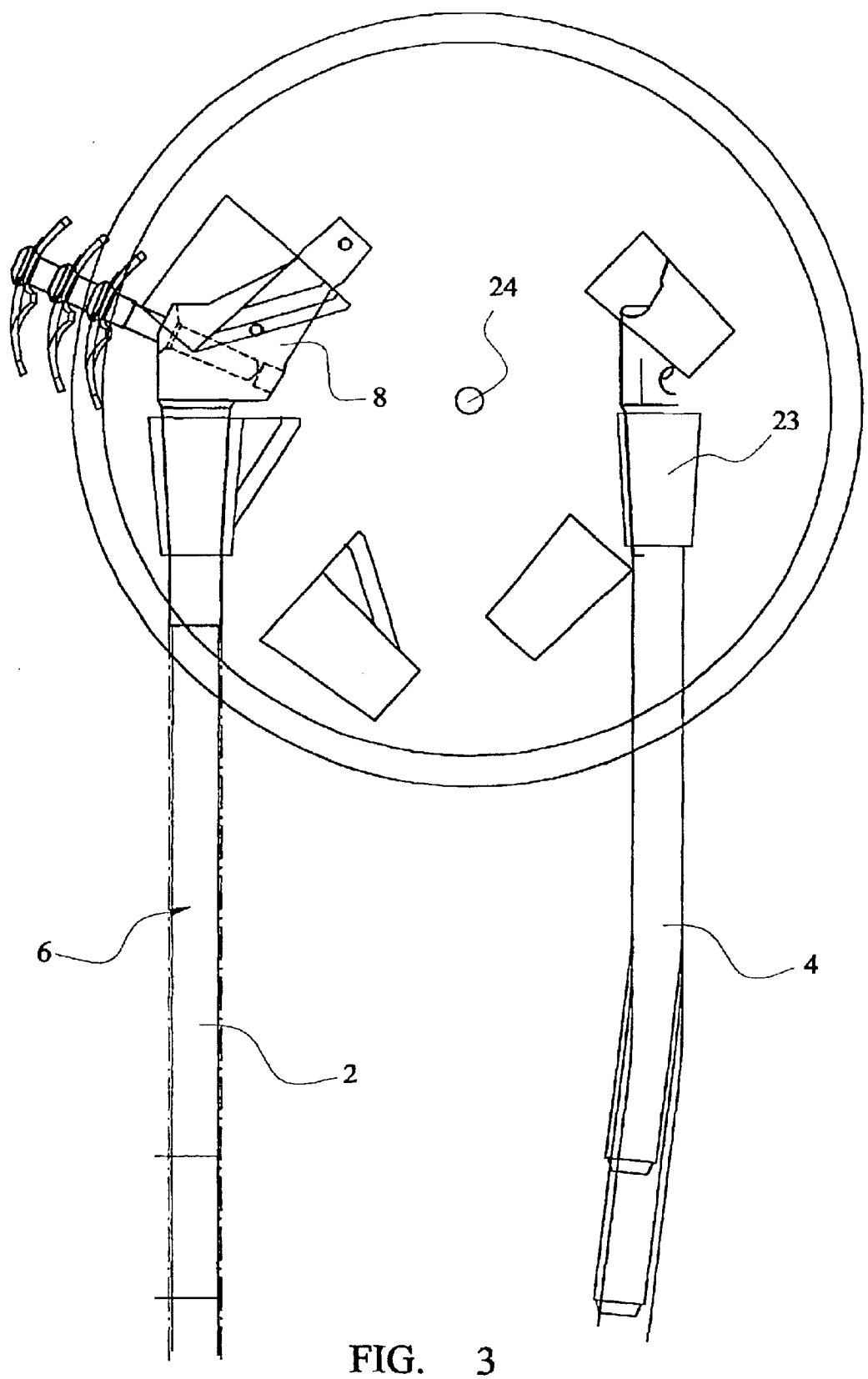
FIG. 3 is a view of a template according to the invention which consists of the first and second parts shown in FIGS. 2 and 3.

FIG. 3 shows the first and second template parts fastened together by means of a rivet which passes through the pivot point 24 on the second template part. The arrangement of the A-P and M-L views of the prosthesis parts on the first and second template parts is such that, when the A-P view of one of the three prosthesis parts on the second template part is located over the A-P view of the first prosthesis part on the first template part, the M-L view of that same prosthesis part on the second template part is located over the M-L view of the first prosthesis part on the first template part.

Changes in the configuration of the prosthesis can be represented by rotating the second prosthesis part relative to the first prosthesis part, to cause the A-P and M-L views of a different one of the three prosthesis parts on the second template part to be aligned with the A-P and M-L views of the first prosthesis part on the first template part.

What is claimed is:

1. A template for use in matching parts of a modular joint prosthesis component to an image of a bone in which the prosthesis component is to be implanted, the prosthesis component comprising a first part and a second part which are fitted together to assemble the prosthesis component for implantation, which comprises:
   a. a first template part which bears an image of the first part of the prosthesis component, and
   b. a second template part which bears images of a plurality of the second parts of the prosthesis component, each of the second parts being a sleeve having a through bore in which, in the assembled prosthesis component, the first part of the prosthesis component can be received, in which the second template part is connected to the first template part but can be moved relative to it so that the images of the second parts of the prosthesis component are aligned sequentially in relation to the image of the first template part to form a composite image of the prosthesis component, one of the template parts overlying the other of the template parts and being transparent so that the image on the said other template part is visible through the overlying template part when the images on the template parts are aligned.

2. A template as claimed in claim 1, in which the first template part bears images of two views of the first part of the prosthesis component, and in which the second template part bears images of two views of the second parts of the prosthesis component.

3. A template for use in matching parts of a modular joint prosthesis component to an image of a bone in which the prosthesis component is to be implanted, the prosthesis component comprising a first part and a second part which are fitted together to assemble the prosthesis component for implantation, which comprises:

a. a first template part which bears images of two views of the first part of the prosthesis component, and b. a second template part which bears images of two views of each of a plurality of the second parts of the prosthesis component, in which the second template part is connected to the first template part but can be moved relative to it so that the images of the views of the second parts of the prosthesis component are positioned sequentially in relation to the images of the corresponding views of the first template part to form composite images of the two views of the assembled prosthesis component.

4. A template as claimed in claim 3, in which one of the template parts overlies the other of the template parts and is transparent, so that the image on the said other template part is visible through the overlying template part when the images on the template parts are aligned.

5. A template as claimed in claim 1 or claim 3, in which the second template part is mounted for rotation relative to the first template part.

6. A template as claimed in claim 2 or claim 3, in which the second template part is mounted for rotation relative to the first template part, and in which the images of the views of the second parts of the prosthesis component are arranged approximately equidistant from the axis of rotation of the second template part.

7. A template as claimed in claim 2 or claim 3, in which the images of the first template part are elevational views along the medial-lateral and anterior-posterior axes respectively.

8. A template as claimed in claim 1 or claim 3, which includes a third template part which bears images of a plurality of third parts of the prosthesis component.

9. A template as claimed in claim 8, in which the third template part is connected to the first template part but can be moved relative to it, so that the images of the third parts of the prosthesis component are positioned sequentially in relation to the image of the first template part to form a composite image of the prosthesis component.

10. A kit for preparing a prosthesis component for implantation in a bone, which comprises a template as claimed in claim 1 or claim 3 and a prosthesis component which comprises a first part and a second part which are fitted together to assemble the prosthesis component for implantation, the first part corresponding to the image which is carried by the first template part, and the second part corresponding to one of the images which is carried by the second template part.

* * * * *